(12) United States Patent
Geng et al.

(10) Patent No.: US 11,067,570 B2
(45) Date of Patent: Jul. 20, 2021

(54) BIO-DETECTION CHIP AND DETECTION METHOD ASSOCIATED THEREWITH

(71) Applicants: BEIJING BOE OPTOELECTRONICS TECHNOLOGY CO., LTD., Beijing (CN); BOE TECHNOLOGY GROUP CO., LTD., Beijing (CN)

(72) Inventors: Yue Geng, Beijing (CN); Peizhi Cai, Beijing (CN); Fengchun Pang, Beijing (CN); Le Gu, Beijing (CN)

(73) Assignees: BEIJING BOE OPTOELECTRONICS TECHNOLOGY CO., LTD., Beijing (CN); BOE TECHNOLOGY GROUP CO., LTD., Beijing (CN)

(*) Notice: Subject to any disclaimer, the term of this patent is extended or adjusted under 35 U.S.C. 154(b) by 361 days.

(21) Appl. No.: 16/095,023

(22) PCT Filed: Apr. 23, 2018

(86) PCT No.: PCT/CN2018/084088
§ 371 (c)(1),
(2) Date: Oct. 19, 2018

(87) PCT Pub. No.: WO2018/210104
PCT Pub. Date: Nov. 22, 2018

(65) Prior Publication Data
US 2020/0348292 A1   Nov. 5, 2020

(30) Foreign Application Priority Data
May 17, 2017 (CN) .......................... 201710348447.1

(51) Int. Cl.
*G01N 33/543* (2006.01)
*B01L 3/00* (2006.01)
*G01N 21/78* (2006.01)

(52) U.S. Cl.
CPC .... *G01N 33/5438* (2013.01); *B01L 3/502715* (2013.01); *G01N 21/78* (2013.01);
(Continued)

(58) Field of Classification Search
None
See application file for complete search history.

(56) References Cited

U.S. PATENT DOCUMENTS 6,169,394 B1    1/2001   Frazier et al.
8,980,198 B2 *  3/2015   Srinivasan ............... B03C 5/02
                                                      422/504

(Continued)

FOREIGN PATENT DOCUMENTS

CN        1912625 A      2/2007
CN      101149371 A      3/2008
(Continued)

OTHER PUBLICATIONS

Shen et al., EWOD microfluidic systems for biomedical applications, 2014, Microfluid Nanofluid, vol. 16, p. 965-987 (Year: 2014).*
(Continued)

*Primary Examiner* — Jennifer Wecker
*Assistant Examiner* — Kathryn Elizabeth Limbaugh
(74) *Attorney, Agent, or Firm* — Calfee, Halter Griswold LLP

(57) ABSTRACT

The present disclosure relates to a bio-detection chip and a detection method associated therewith. The bio-detection chip includes an upper substrate, a lower substrate, a reference electrode, a driving electrode, and a first dielectric
(Continued)

layer, a first hydrophobic layer, a second hydrophobic layer and a second dielectric layer disposed successively between the reference electrode and the driving electrode. The bio-detection chip further includes a plurality of micro-capsules arranged between the first hydrophobic layer and the second hydrophobic layer. Each micro-capsule encapsulates a plurality of charged microspheres, and surfaces of the charged microspheres have a first biomolecule for specifically binding with a second biomolecule that enters the bio-detection chip so as to give rise to a color change. The charged microspheres move close to the upper substrate when a voltage is applied between the reference electrode and the driving electrode. As such, a result of biomolecule detection may be observed intuitively.

20 Claims, 5 Drawing Sheets

(52) U.S. Cl.
CPC ............... *B01L 2300/0645* (2013.01); *B01L 2300/0819* (2013.01); *B01L 2300/0861* (2013.01); *B01L 2300/165* (2013.01); *B01L 2300/168* (2013.01); *B01L 2400/0415* (2013.01)

(56) References Cited

U.S. PATENT DOCUMENTS

| | | | | |
|---|---|---|---|---|
| 2009/0197772 | A1* | 8/2009 | Griffiths | ............ B01L 3/502761 506/9 |
| 2016/0059230 | A1* | 3/2016 | Hsu | ................... B01L 3/502784 204/602 |

FOREIGN PATENT DOCUMENTS

| | | | | |
|---|---|---|---|---|
| CN | 104364649 A | 2/2015 | | |
| CN | 104668003 A | 6/2015 | | |
| CN | 105233887 A | 1/2016 | | |
| CN | 105466985 A | 4/2016 | | |
| CN | 105572398 A | 5/2016 | | |
| CN | 107159327 A | 9/2017 | | |
| GB | 2533951 A | * | 7/2016 | ........... G02B 26/005 |
| JP | 2005249480 A | 9/2005 | | |

OTHER PUBLICATIONS

Lin et al., Formation of Droplets Interface Bilayer by Coplanar EWOD Device, 2011, Proceedings of the 2011 6th IEEE International Conference on Nano/Micro Engineered and Molecular Systems, p. 964-967 (Year: 2011).*

Rosenholtz et al., The effect of background color on asymmetries in color search, 2004, Journal of Vision, vol. 4, p. 224-240 (Year : 2004).*

Search Report and Written Opinion for International Application No. PCT/CN2018/084088 dated Jul. 6, 2018.

First Office Action for Chinese Patent Application No. 201710348447.1 dated Nov. 2, 2018.

* cited by examiner

BIO-DETECTION CHIP AND DETECTION METHOD ASSOCIATED THEREWITH

RELATED APPLICATION

The present application is the U.S. national phase entry of PCT/CN2018/084088, with an international filling date of Apr. 23, 2018, which claims the priority of the Chinese patent application No. 201710348447.1 filed on May 17, 2017, the entire disclosures of which are incorporated herein by reference.

FIELD

The present disclosure relates to the field of bio-detection, particularly to a bio-detection chip and a detection method associated therewith.

BACKGROUND

Current biomolecule detection is performed on a corresponding detection chip, such as protein detection, antigen antibody detection, enzyme detection, gene detection etc. The detection method thereof is: firstly immobilizing a large number of different probe molecule spots onto respective detection sites of the chip, and then inletting the fluorescently labeled biomolecule solution that is to be detected into the chip. If a biomolecule to be detected has a specific binding reaction with a probe of a certain site, the structure or the type of the biomolecule to be detected may be determined by detecting the released fluorescence signal. The detection result of the detection method has a relatively high accuracy, however, the structure or the type of the biomolecule to be detected may only be determined through the fluorescence detection process, which has a low intuitiveness. Moreover, the current biomolecule detection chip is generally used for a single time, fewer species of the biomolecules to be detected may be detected each time, which may result in great increase in the cost of consumables for the detection, and is not benefit for popularization and promotion of the biomolecule detection technology.

Therefore, how to simplify a detection process of biomolecules and reduce the cost of biomolecule detection is a technical problem that needs to be solved by those skilled in the art.

SUMMARY

Embodiments of the present disclosure provide a bio-detection chip and a detection method associated therewith, for simplifying the detection process of biomolecules and reducing the cost of biomolecule detection.

In one embodiment, an embodiment of the present disclosure provides a bio-detection chip. The bio-detection chip comprises an upper substrate and a lower substrate disposed opposite to each other, a reference electrode, a driving electrode, a first dielectric layer, a second dielectric layer, a first hydrophobic layer and a second hydrophobic layer. The reference electrode is formed on a side of the upper substrate facing the lower substrate. The driving electrode is formed on a side of the lower substrate facing the upper substrate. The first dielectric layer, the first hydrophobic layer, the second hydrophobic layer and the second dielectric layer are disposed successively between the reference electrode and the driving electrode. The bio-detection chip further comprises a plurality of micro-capsules arranged between the first hydrophobic layer and the second hydrophobic layer. The micro-capsule encapsulates a plurality of charged microspheres, and surfaces of the charged microspheres have a first biomolecule for specifically binding with a second biomolecule that enters the bio-detection chip so as to give rise to a color change. One of the first biomolecule and the second biomolecule is a biomolecule to be detected. The charged microspheres move close to the upper substrate when a voltage is applied between the reference electrode and the driving electrode.

In some embodiment, the bio-detection chip further comprises a plurality of baffle walls disposed between the first hydrophobic layer and the second hydrophobic layer. The baffle walls divide a space between the upper substrate and the lower substrate into a plurality of sub-spaces. There is a gap between two adjacent ones of the baffle walls. The micro-capsules are filled in the sub-spaces. A diameter of the micro-capsules is equal to a height of the baffle walls and larger than a width of the gap.

In some embodiment, the driving electrode comprises a plurality of sub-electrodes. Each sub-electrode corresponds to one or more of the plurality of sub-spaces. The bio-detection chip further comprises controllable switches in one-to-one correspondence with respective sub-electrodes. The switches may be switch transistors.

In some embodiments, orthographic projections of the baffle walls on the lower substrate are arranged around orthographic projections of the sub-electrodes on the lower substrate. A shape of the sub-electrode may be a regular hexagon.

In some embodiments, the surface of a micro-capsule has a plurality of micropores. The microspheres are white, and the first biomolecule comprises a plurality of joints for specifically binding with the second biomolecules.

In some embodiments, a diameter of the micro-capsules is in a range of 50~200 µm.

In some embodiments, the upper substrate has a set of sample inlet and sample outlet. The sample inlet is arranged for leading-in of a sample solution containing the second biomolecule. The sample outlet is arranged for leading-out of the sample solution. The upper substrate may be a transparent substrate.

In some embodiments, the surfaces of the charged microspheres in the micro-capsules filled in different sub-spaces have respective first biomolecules arranged for specifically binding with different biomolecules.

In the other embodiment, an embodiment of the present disclosure provides a detection method using the bio-detection chip as mentioned above or elsewhere herein. The method comprises: leading a sample solution of the second biomolecule with a dye label into the bio-detection chip; applying a voltage signal between the reference electrode and the driving electrode after the sample solution flows through the plurality of micro-capsules; and determining information of the biomolecules to be detected based on the micro-capsules for which color change occurs.

In some embodiments, the method further comprises, after the sample solution flowing through the plurality of micro-capsules, and before applying a voltage signal between the reference electrode and the driving electrode, leading a sample solution for which no specific binding occurs out of the bio-detection chip.

BRIEF DESCRIPTION OF DRAWINGS

The above and other embodiments of the present disclosure will now be described in more detail with reference to the accompanying drawings in which.

DETAILED DESCRIPTION

The specific embodiments of a bio-detection chip and a detection method associated therewith provided by the embodiments of the present disclosure are described in detail below with reference to the accompanying drawings.

Figure 1:
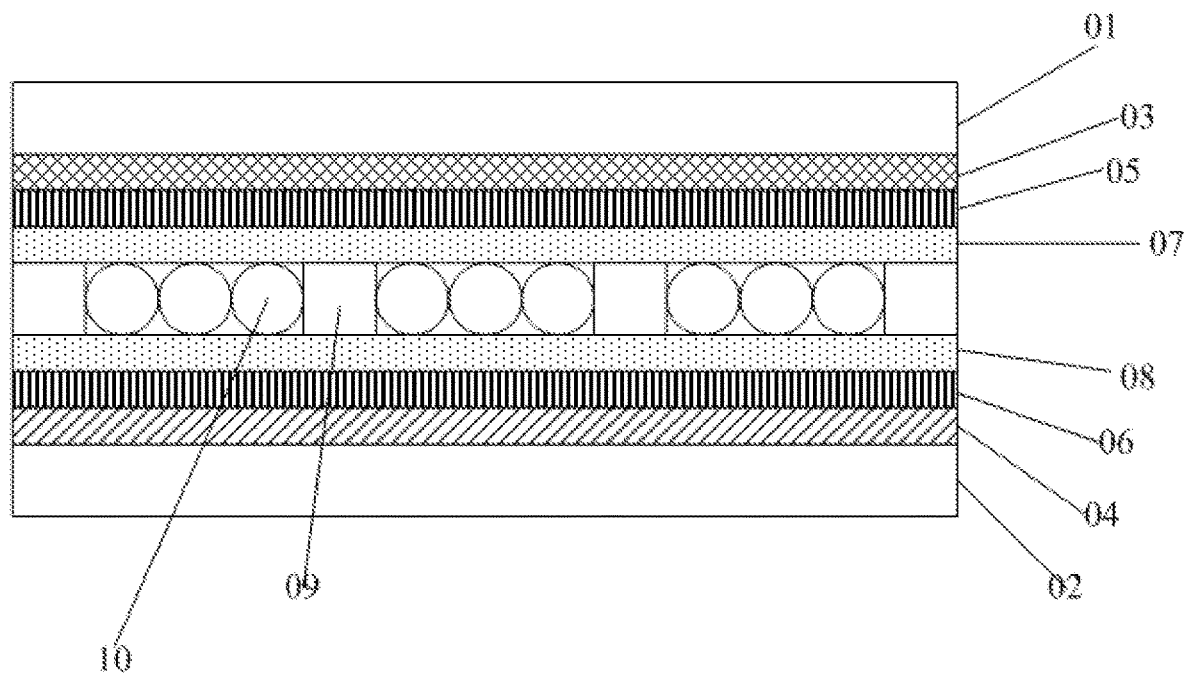
FIG. 1 is a schematic view of structure of a bio-detection chip according to an embodiment of the present disclosure.

FIG. 1 shows a bio-detection chip according to an embodiment of the present disclosure. The bio-detection chip comprises: an upper substrate 01 and a lower substrate 02 disposed opposite to each other, a reference electrode 03, a driving electrode 04, a first dielectric layer 05, a second dielectric layer 06, a first hydrophobic layer 07 and a second hydrophobic layer 08. The reference electrode 03 is formed on a side of the upper substrate 01 that faces the lower substrate 02. The driving electrode 04 is formed on a side of the lower substrate 02 that faces the upper substrate 01. The first dielectric layer 05, the first hydrophobic layer 07, the second hydrophobic layer 08 and the second dielectric layer 06 are disposed successively between the reference electrode 03 and the driving electrode 04. Exemplarily, the first dielectric layer 05 is located on a side of the reference electrode 03 that faces the lower substrate 02. The first hydrophobic layer 07 is located on a side of the first dielectric layer 05 that faces the lower substrate 02. The second dielectric layer 06 is located on a side of the driving electrode 04 that faces the upper substrate 01. The second hydrophobic layer 08 is located on a side of the second dielectric layer 06 that faces the upper substrate 01.

In some embodiments, the materials of the upper and lower substrates may be glass, silicon and the like. The driving electrode may be formed by depositing and etching on the lower substrate. The material of the driving electrode may be ITO (indium tin oxide). Because ITO has better transparency, it is convenient for observing colors. Afterwards, the dielectric layer and the hydrophobic layer may be formed. The material of the dielectric layer may be silicon oxide, silicon nitride etc., and the material of the hydrophobic layer may be a low surface energy material such as PTFE (polytetrafluoroethylene).

The bio-detection chip further comprises a plurality of micro-capsules arranged between the first hydrophobic layer and the second hydrophobic layer. In some embodiments, a layer of micro-capsules may be laid between the first hydrophobic layer and the second hydrophobic layer. Exemplarily, a micro-capsule may comprise a capsule membrane wall shell made from natural polymer materials (e.g., gelatin, acacia, alginate, etc.) or synthetic polymer materials (e.g., polyamide, polyamino acid, etc.). In some embodiments, substances with bioactivity may be encapsulated within the capsule membrane wall shell to form, for example, a spherical micro-capsule.

The micro-capsule encapsulates a plurality of charged microspheres, a surface thereof having a first biomolecule (e.g., a known biomolecule) for specifically binding with a second biomolecule (e.g., a biomolecule to be detected) that enters the bio-detection chip so as to give rise to a change in color. The charged microsphere may change to a labeled color of the biomolecule to be detected. The charged microsphere may move close to the upper substrate when a voltage is applied between the reference electrode and the driving electrode. Thus, a color signal of the charged microsphere with a color change may be observed from the top of the chip (e.g., through the upper substrate), so as to obtain information of the biomolecules to be detected.

In some embodiment, the bio-detection chip further comprises a plurality of baffle walls. Each baffle wall 09 is disposed between the first hydrophobic layer 07 and the second hydrophobic layer 08, and each baffle wall 09 divides the space between the upper substrate 01 and the lower substrate 02 (i.e., between the first hydrophobic layer 07 and the second hydrophobic layer 08) into a plurality of sub-spaces. In some embodiments, the baffle walls may be formed by depositing and etching on the second hydrophobic layer. The material of the baffle wall may be silicon nitride, silicon oxide, resin, etc.

Figure 2:
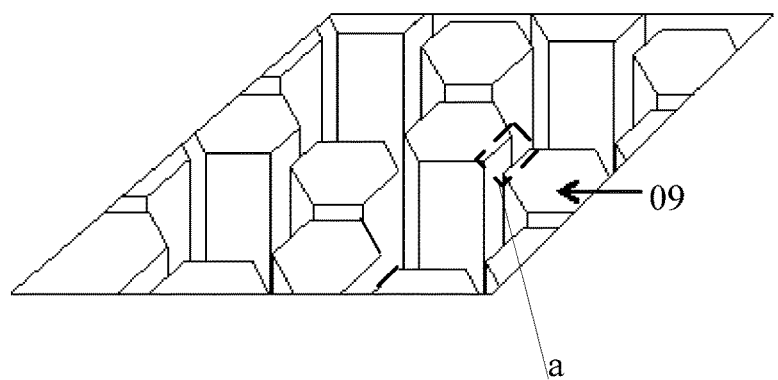
FIG. 2 is a schematic view of arrangement of baffle walls according to an embodiment of the present disclosure.

FIG. 2 shows a schematic illustration of baffle walls formed according to an embodiment of the present disclosure. As shown in FIG. 2, a plurality of baffle walls divides the entire space into a plurality of sub-spaces. There is a gap a between two adjacent baffle walls 09 that surround a sub-space. Each sub-space may be filled with a plurality of micro-capsules 10 for which color change may occur due to specific binding between biomolecules. In some embodiments, a diameter of a micro-capsule 10 may be equal to a height of the baffle wall 09, but larger than a width of the gap a. As such, the gap between the baffle walls is smaller than the diameter of the micro-capsule, which may ensure that the micro-capsules cannot move in different sub-spaces through the gaps, while liquid may be allowed to flow among the sub-spaces through the gaps of the baffle walls.

In the above bio-detection chip provided by the embodiment of the present disclosure, the micro-capsules in each sub-space may undergo a color change as a result of specific binding of a known biomolecule with a biomolecule to be detected, for example, changing into the labeled color of the biomolecule to be detected. In this way, by applying a voltage to the driving electrode and the reference electrode, the micro-capsule may be close to the surface of the upper substrate so as to exhibit its color change. Thus, the color change of the micro-capsules may be observed directly from the top of the bio-detection chip, so that intuitive observation of detection result for biomolecule detection may be achieved, thereby determining the structure or type information of the biomolecules to be detected. Compared with the relevant art, fluorescence detection is unnecessary for the solution according to an embodiment of the present disclosure, simplifying the detection process of biomolecules. Moreover, the micro-capsules in the bio-detection chip of the embodiment of the present disclosure are replaceable, so that the bio-detection chip is reusable, which reduces detection cost. In addition, the bio-detection chip may be manufactured using the existing photolithography process, of which the manufacturing method is simple.

Figure 3:
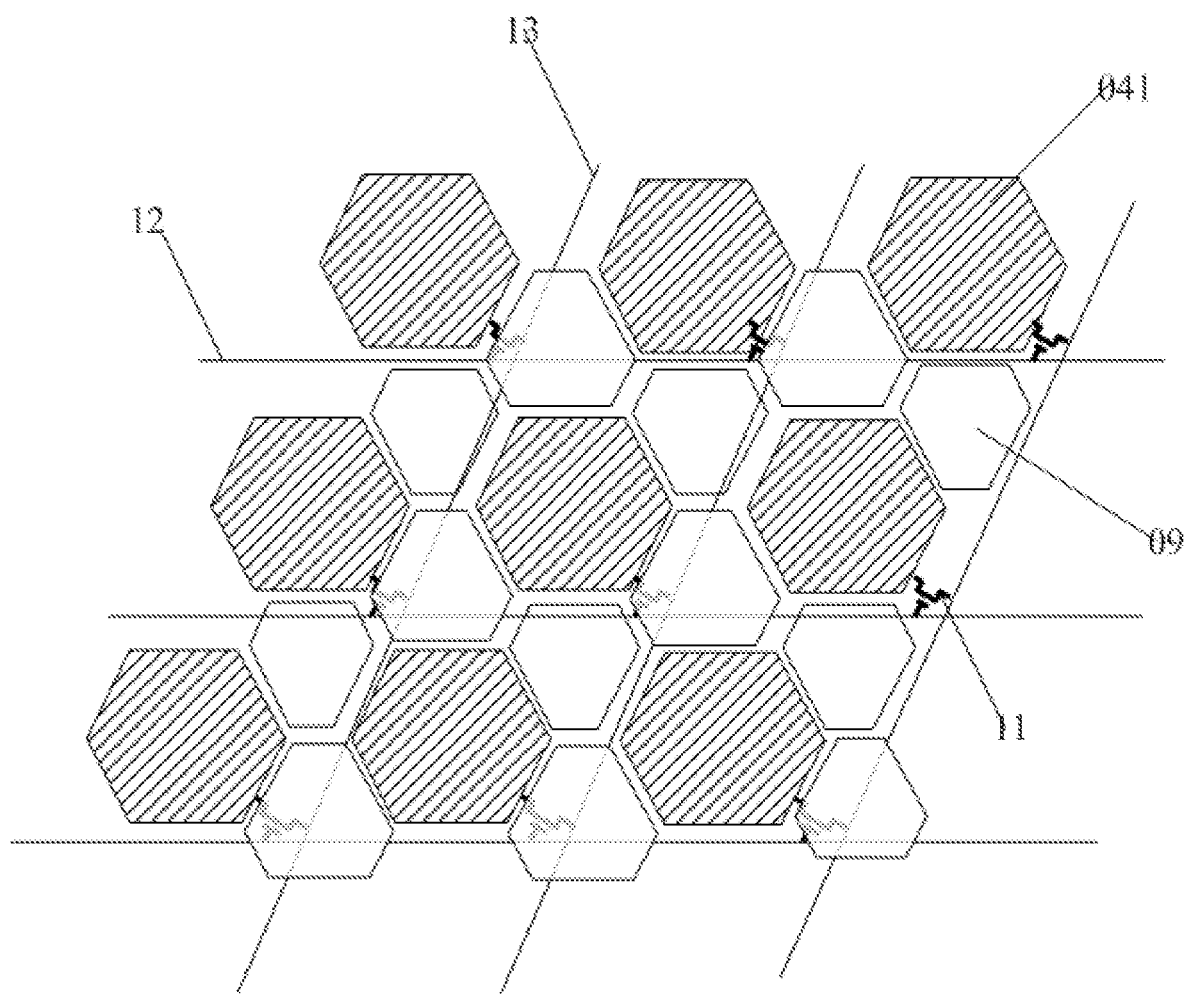
FIG. 3 is a schematic view of arrangement of sub-electrodes according to an embodiment of the present disclosure.

FIG. 3 shows an exemplary illustration of a structure of the bio-detection chip provided according to an embodiment of the present disclosure. As shown in the figure, the driving electrode comprises a plurality of sub-electrodes 041. The sub-electrodes 041 may be arranged in a matrix. In some embodiments, the bio-detection chip may further comprise: switches 11 in one-to-one correspondence with respective sub-electrodes 041, a plurality of control lines 12 extending along a first direction and a plurality of signal lines 13 extending along a second direction intersecting with the first direction. In one embodiment, each control line 12 is connected with a control terminal of one or more switches 11, and each signal line 13 is connected with an input terminal of one or more switches 11. An output terminal of each switch 11 is connected with a corresponding sub-electrode 041. A switch 11 may, under the control of the corresponding control line 12, input a signal on a respective signal line 13 into a corresponding sub-electrode 041 so as to generate a driving voltage. In one embodiment, each switch 11 may be controlled individually.

In the bio-detection chip provided by an embodiment of the present disclosure, control on a per region basis may be achieved by dividing a driving electrode into a plurality of sub-electrodes, and then arranging switches in one-to-one correspondence with respective sub-electrodes to control biomolecule detection in respective regions corresponding to one or more sub-electrodes. In addition, as shown in FIG. 3, the baffle walls 09 may be arranged so that the orthographic projections of adjacent baffle walls on the lower substrate 02 are arranged around the orthographic projections of the sub-electrodes 041 on the lower substrate 02, i.e., the sub-electrodes 041 may correspond to respective sub-spaces divided by the baffle walls, e.g., sub-spaces being separated or defined by corresponding baffle walls. This makes a region corresponding to each sub-electrode be the region planed for detecting biomolecules. Through arrangement of the baffle walls, a region for one sub-electrode may correspond to a detection region enclosed the baffle walls. Furthermore, the biomolecule detection may be performed in a region by controlling powering of a corresponding sub-electrode via a switch. In one embodiment, switches may be controlled individually, so as to enable them to control each sub-electrode accurately, thereby allowing controlling each detection region accurately.

In one embodiment, a switch may be implemented with a switch transistor. Exemplarily, a gate of the switch transistor is connected with a corresponding control line, a source of it is connected with a corresponding signal line, and a drain of it is connected with corresponding sub-electrode(s). When the biomolecule detection is performed, a switch transistor corresponding to one or more sub-electrodes in a detection region may be controlled to turn on through a control line, so as to output a voltage signal on a signal line to the corresponding sub-electrodes, so as to implement biomolecule detection in the region corresponding to the sub-electrode.

In one embodiment, as shown in FIG. 3, a shape of a sub-electrode 041 may be a regular hexagon. As would be appreciated, the sub-electrode 041 may also be set in other appropriate shapes, such as round, rectangle etc. In a practical application, the shape of a sub-electrode may be adapted to that of the detection region. Correspondingly, a cross section shape of a baffle wall may also be set in various shapes. As shown in FIG. 3, the shape of the orthographic projection of the baffle wall 09 on the lower substrate may be a hexagon. In a practical application, the baffle wall may also be set in other types of cross section shapes, and is not limited thereto.

Figure 4:
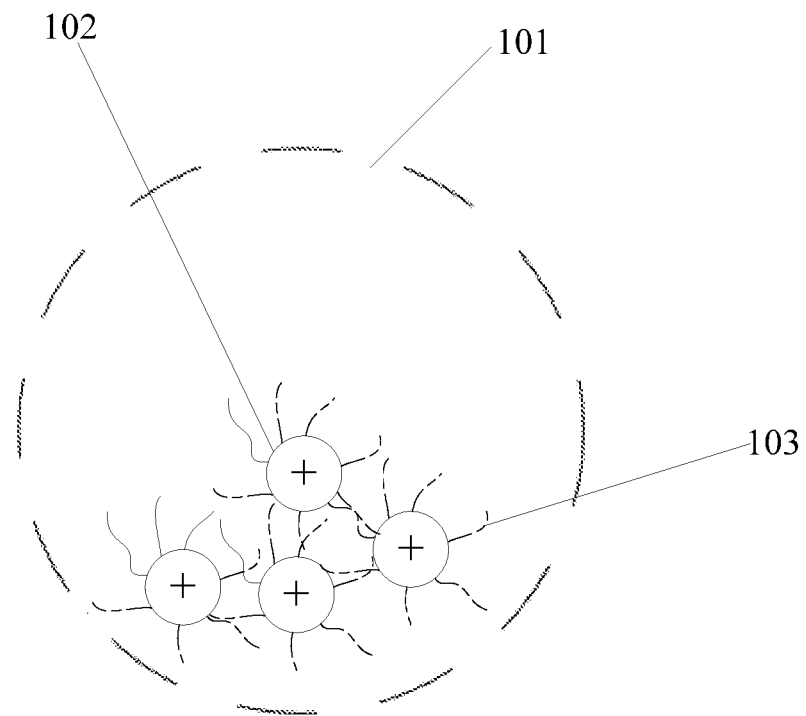
FIG. 4 is a schematic view of structure of a micro-capsule according to an embodiment of the present disclosure.

FIG. 4 shows a schematic view of structure of a micro-capsule according to an embodiment of the present disclosure. As shown in the figure, the surface of a micro-capsule 10 has a plurality of micropores 101. The micro-capsule 10 is provided with a plurality of microspheres 102 which are white and charged. The surface of the microsphere 102 has a plurality of joints 103 for specifically binding. The joint 103 may be known biomolecule or biomolecule to be detected. In some embodiments, the micropores are arranged to allow free entry and exit of biomolecules with dye labels. The surface of the white charged microsphere encapsulated in the micro-capsule may be treated chemically so as to connect joints of different structure and types, such as antigen, antibody, aptamer etc. These joints can only specifically bind with one kind of other biomolecules. In some embodiments, different sub-spaces formed by baffle walls may be filled with micro-capsules, which have charged microspheres with joints of different structures and types for detecting different biomolecules.

In an exemplary scene where protein detection is performed, various known protein antigen molecules may be immobilized or adsorbed on surfaces of microspheres within micro-capsules. Afterwards, for each known protein antigen molecule, a position of a micro-capsule comprising microspheres associated with that known protein antigen molecule in the bio-detection chip, e.g., in which sub-space the micro-capsule is, is recorded. Alternatively, the names of the known protein antigen molecules immobilized or adsorbed on the surfaces of microspheres within micro-capsules at different positions (e.g., in respective sub-spaces) of the bio-detection chip may also be recorded. The antibody to be detected may be labeled using a dye, formulated into a solution, and then be allowed to flow into the bio-detection chip. When the solution flows through the bio-detection chip, for example, flowing through each micro-capsule, only one kind of known protein antigen molecules will specifically bind with the antibody to be detected. Thus, the microspheres with respective immobilized known protein antigen molecules would change to the labeled color of the antibody to be detected. Afterwards, the unreacted antibody solution, for example for which no specific binding occurs, will be cleaned out of the bio-detection chip. The antibody to be detected may be determined based on the site where color change occurs.

Alternatively, in another exemplary scene where protein detection is performed, the antibody to be detected may be immobilized on surfaces of microspheres within micro-capsules. And then, various known protein antigen molecules are differently labeled using dyes, and formulated into a solution to flow into the bio-detection chip. When the solution flows through each micro-capsule, only one kind of known protein antigen molecules specifically bind with the antibody to be detected. After the specific binding occurs, the color of the surfaces of microspheres changes with the color of the bound protein antigen molecules. Afterwards, the unreacted solution containing the antigen molecules will be cleaned out of the chip. The antibody to be detected may be determined based on the color exhibited by the microsphere.

FIGS. 5A-5D show schematic views of a biomolecule detection process provided by embodiments of the present disclosure.

Figure 5A:
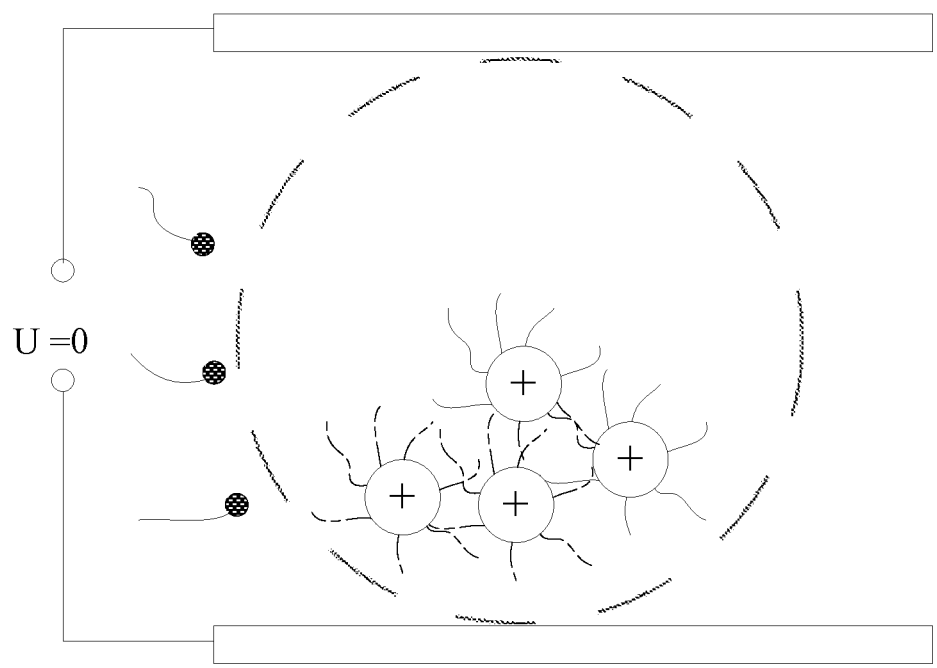
FIG. 5A is a schematic view of a biomolecule detection process according to an embodiment of the present disclosure.

As shown in FIG. 5A, when no voltage is applied between a reference electrode and a driving electrode, a sample solution of biomolecules that is to be detected and with dye labels is led in the bio-detection chip. The sample solution flows through all the micro-capsules. At this time, the biomolecules in the sample solution may enter the micro-capsules through the micropores on the micro-capsules and be in contact with the white charged microspheres in the micro-capsules.

Figure 5B:
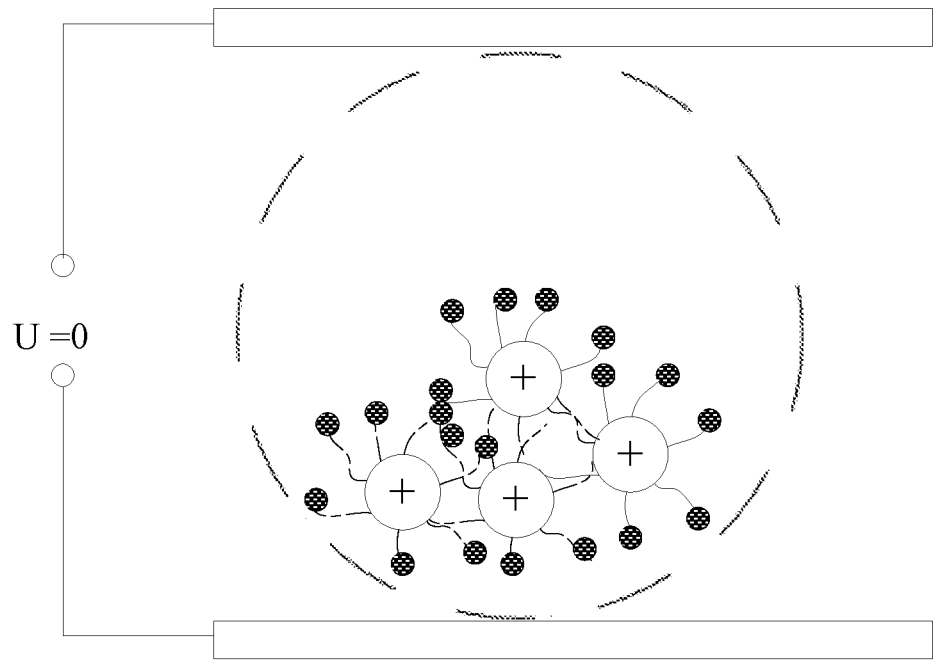
FIG. 5B is a schematic view of a biomolecule detection process according to an embodiment of the present disclosure.
Figure 5C:
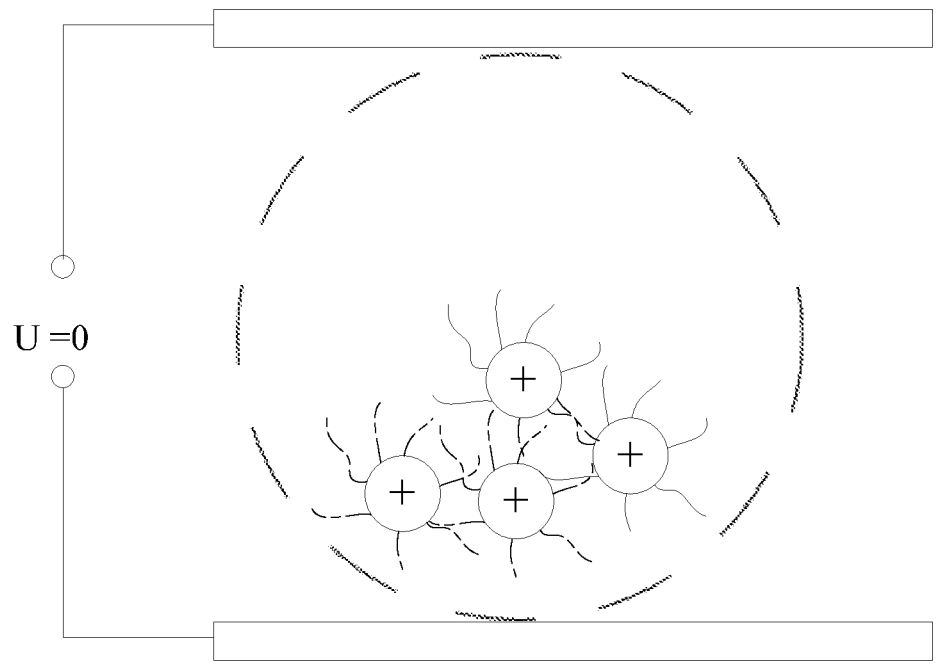
FIG. 5C is a schematic view of a biomolecule detection process according to an embodiment of the present disclosure.

As shown in FIG. 5B, since the biomolecules to be detected specifically bind with the joints on the charged microspheres, the surfaces of these charged microspheres change from white to corresponding labeled color of the biomolecules to be detected. As shown in FIG. 5C, if the biomolecules to be detected do not specifically bind with the joints on the charged microspheres, the surfaces of the charged microspheres are still white. In some embodiments, in the event that the micro-capsules in respective sub-spaces divided by the baffle walls may have charged microspheres with different joints, the surfaces of the charged microspheres in some of the sub-spaces may possibly change to the labeled color, while the charged microspheres in other sub-spaces are still white.

Figure 5D:
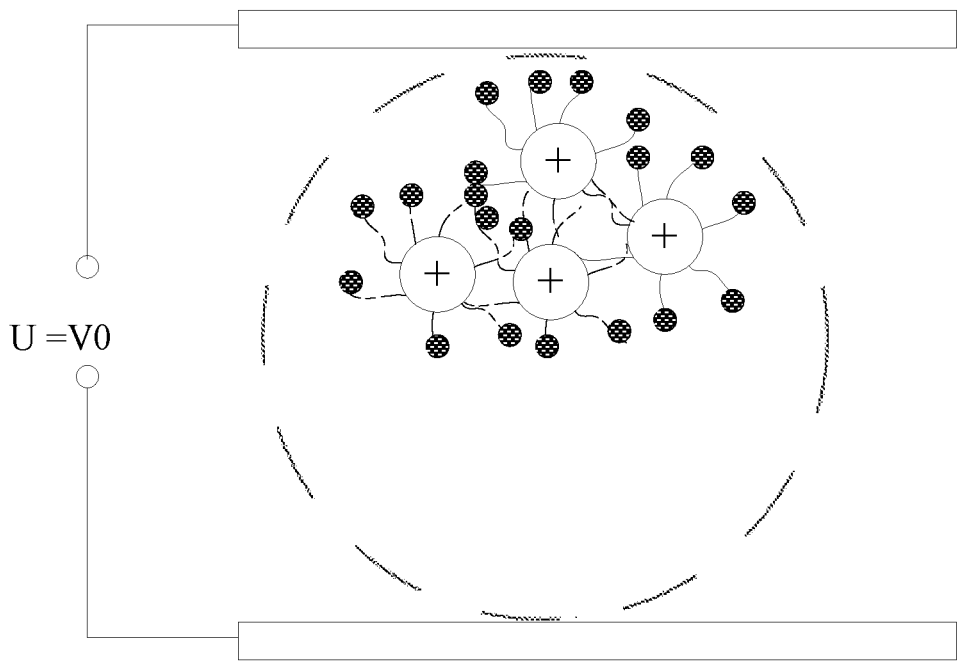
FIG. 5D is a schematic view of a biomolecule detection process according to an embodiment of the present disclosure.

Afterwards, a voltage is applied between the reference electrode and the driving electrode through for example switch control. As shown in FIG. 5D, the charged microspheres in a micro-capsule will move in the micro-capsule toward the surface close to the upper substrate. In some embodiments, the upper substrate is a transparent substrate, hence, the color exhibited by the microspheres may be observed intuitively, so as to detect the biomolecules to be detected.

In one embodiment, a diameter of the micro-capsules may be in a range of tens to hundreds of μm. Exemplarily, the diameter of a micro-capsule may be set in a range of 50~200 μm.

In one embodiment, the upper substrate has a set of sample inlet and sample outlet. The sample inlet is arranged for leading-in of the sample solution, and the sample outlet is arranged for leading-out of the sample solution. Exemplarily, the bio-detection chip may dispose a pair of sample inlet and sample outlet on the upper substrate for implementing leading-in and leading-out of the detection solution.

It could be understood that in some other embodiments, similarly, the detection of the biomolecules to be detected may be fulfilled by immobilizing biomolecules to be detected on the surfaces of microspheres and bringing known biomolecules into the solution.

Figure 6:
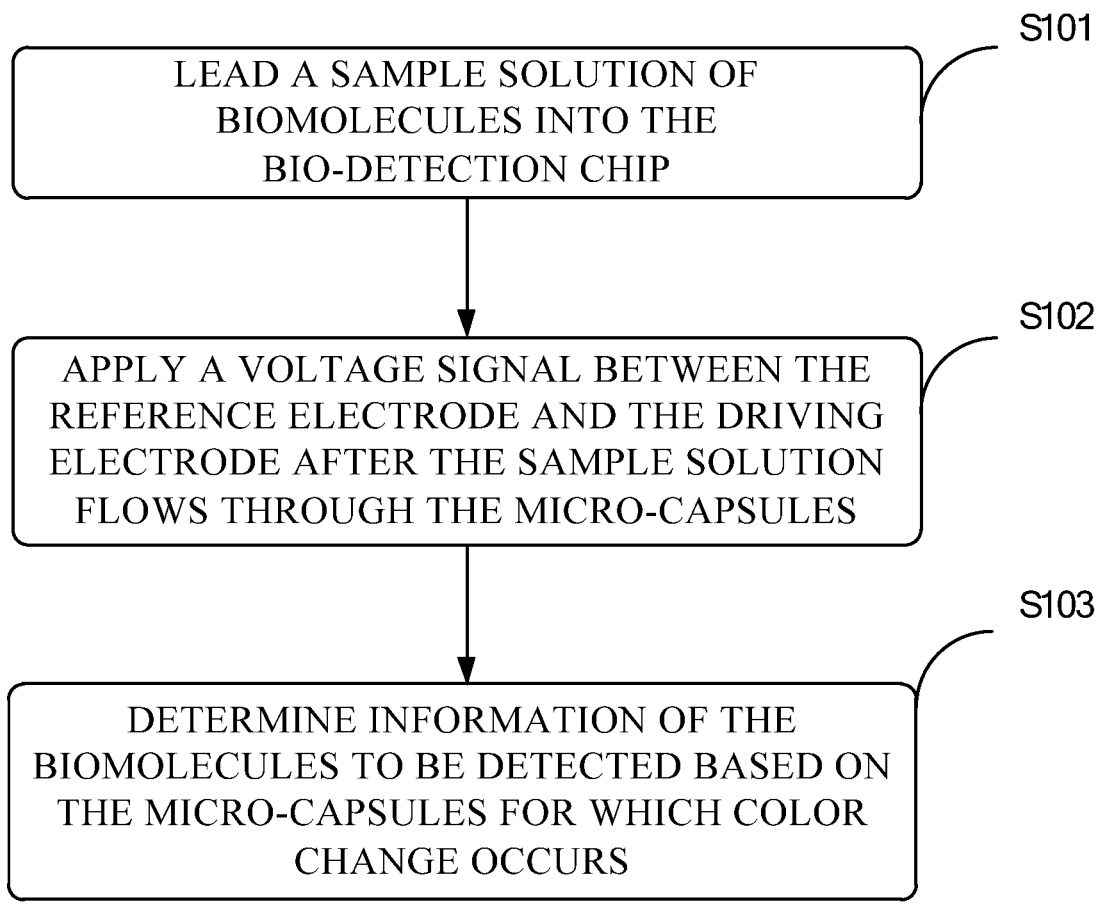
FIG. 6 is a flow chart of a bio-detection method according to an embodiment of the present disclosure.

FIG. 6 shows a detection method using a bio-detection chip provided by an embodiment of the present disclosure. As shown in FIG. 6, the method may comprise:

S101, leading a sample solution of biomolecules with a dye label into the bio-detection chip. The biomolecules with the dye label may be biomolecules to be detected or known biomolecules.

S102, applying a voltage signal between the reference electrode and the driving electrode after the sample solution flows through the plurality of micro-capsules;

S103, determining information of the biomolecules to be detected based on micro-capsules for which color change occurs. The biomolecules to be detected may be biomolecules in the sample solution or biomolecules immobilized on the surfaces of microspheres.

In the above detection method provided by an embodiment of the present disclosure, color change of micro-capsules may be observed intuitively, and information of the biomolecules to be detected, for example, the structure or type information of the biomolecules to be detected, may be determined based on the micro-capsules for which color change occurs. With respect to the relevant art, fluorescence detection is unnecessary for approaches according to the embodiments of the present disclosure. This simplifies the detection process of biomolecules.

In some embodiments, the sample solution may be injected into the bio-detection chip through a sample inlet in the upper substrate of the bio-detection chip. In one embodiment, after the sample solution flows through the micro-capsules, and before applying a voltage signal between the reference electrode and the driving electrode, the method further comprises: cleaning out the unreacted sample solution. For example, the sample solution may be led out of the bio-detection chip from the sample outlet. Thus, influence of the unreacted sample solution on the observation to the detection result may be avoided.

In some embodiments, the micro-capsules in the bio-detection chip of the present disclosure are replaceable, so that the bio-detection chip is reusable, which further reduces the detection cost.

Apparently, the skilled person in the art may make various amendments and modifications to the present disclosure without departing from the spirit and the scope of the present disclosure. Thus, provided that these amendments and modifications of the present disclosure belong to the scopes of the claims of the present disclosure and the equivalent technologies, the present disclosure also intends to encompass these amendments and modifications.

The invention claimed is:

1. A bio-detection chip, comprising: an upper substrate and a lower substrate disposed opposite to each other, a reference electrode, a driving electrode, a first dielectric layer, a second dielectric layer, a first hydrophobic layer and a second hydrophobic layer; wherein,
    the reference electrode is formed on a side of the upper substrate facing the lower substrate;
    the driving electrode is formed on a side of the lower substrate facing the upper substrate;
    the first dielectric layer, the first hydrophobic layer, the second hydrophobic layer and the second dielectric layer are disposed successively between the reference electrode and the driving electrode;
    wherein the bio-detection chip further comprises a plurality of micro-capsules arranged between the first hydrophobic layer and the second hydrophobic layer, each of the micro-capsules comprising a capsule membrane wall shell made from natural polymer materials and encapsulating a plurality of charged microspheres within the capsule membrane wall shell, and surfaces of the charged microspheres having a first biomolecule for specifically binding with a second biomolecule that enters the bio-detection chip so as to give rise to a color change, wherein one of the first biomolecule and the second biomolecule is a biomolecule to be detected, and if a voltage is applied between the reference electrode and the driving electrode the charged microspheres move close to the upper substrate; and
    wherein the bio-detection chip further comprises a plurality of baffle walls disposed between the first hydrophobic layer and the second hydrophobic layer, the baffle walls dividing a space between the upper substrate and the lower substrate into a plurality of sub-spaces, with a gap between two adjacent ones of the baffle walls; wherein the micro-capsules are filled in the sub-spaces, such that the baffle walls are configured to ensure that the micro-capsules cannot move in different sub-spaces through the gaps.

2. The bio-detection chip as claimed in claim 1, wherein a diameter of the micro-capsule is equal to a height of the baffle wall and larger than a width of the gap.

3. The bio-detection chip as claimed in claim 2, wherein the surfaces of the charged microspheres in the micro-capsules filled in different sub-spaces have respective first biomolecules arranged for specifically binding with different biomolecules.

4. The bio-detection chip as claimed in claim 3, wherein the upper substrate is a transparent substrate.

5. The bio-detection chip as claimed in claim 2, wherein the upper substrate has a set of sample inlet and sample outlet, the sample inlet being arranged for leading-in of a sample solution containing the second biomolecule, and the sample outlet being arranged for leading-out of the sample solution.

6. The bio-detection chip as claimed in claim 2, wherein the upper substrate is a transparent substrate.

7. The bio-detection chip as claimed in claim 2, wherein the driving electrode comprises a plurality of sub-electrodes, each sub-electrode corresponding to one or more of the plurality of sub-spaces, and the bio-detection chip further comprises: controllable switches in one-to-one correspondence with respective sub-electrodes.

8. The bio-detection chip as claimed in claim 7, wherein orthographic projections of the baffle walls on the lower substrate are arranged around orthographic projections of the sub-electrodes on the lower substrate.

9. The bio-detection chip as claimed in claim 7, wherein the switches are switch transistors.

10. The bio-detection chip as claimed in claim 7, wherein a shape of the sub-electrode is a regular hexagon.

11. The bio-detection chip as claimed in claim 7, wherein the upper substrate has a set of sample inlet and sample outlet, the sample inlet being arranged for leading-in of a sample solution containing the second biomolecule, and the sample outlet being arranged for leading-out of the sample solution.

12. The bio-detection chip as claimed in claim 7, wherein the upper substrate is a transparent substrate.

13. The bio-detection chip as claimed in claim 1, wherein the surface of a micro-capsule has a plurality of micropores being arranged to allow free entry and exit of the second biomolecule, and the microspheres are white, wherein the first biomolecule comprises a plurality of joints for specifically binding with the second biomolecule.

14. The bio-detection chip as claimed in claim 13, wherein the upper substrate has a set of sample inlet and sample outlet, the sample inlet being arranged for leading-in of a sample solution containing the second biomolecule, and the sample outlet being arranged for leading-out of the sample solution.

15. The bio-detection chip as claimed in claim 1, wherein a diameter of the micro-capsules is in a range of about 50 to about 200 μm.

16. The bio-detection chip as claimed in claim 1, wherein the upper substrate has a set of sample inlet and sample outlet, the sample inlet being arranged for leading-in of a sample solution containing the second biomolecule, and the sample outlet being arranged for leading-out of the sample solution.

17. The bio-detection chip as claimed in claim 1, wherein the upper substrate is a transparent substrate.

18. A detection method using the bio-detection chip as claimed in claim 1, comprising:
    leading a sample solution of the second biomolecule with a dye label into the bio-detection chip;
    applying a voltage signal between the reference electrode and the driving electrode after the sample solution flows through the plurality of micro-capsules; and
    determining information of the biomolecules to be detected based on the micro-capsules for which color change occurs.

19. The detection method as claimed in claim 18, wherein after the sample solution flows through the plurality of micro-capsules, and before applying a voltage signal between the reference electrode and the driving electrode, the detection method further comprising:
    leading a sample solution for which no specific binding occurs out of the bio-detection chip.

20. The detection method as claimed in claim 18, wherein the surface of a micro-capsule has a plurality of micropores being arranged to allow free entry and exit of the second biomolecule, and the microspheres are white, wherein the first biomolecule comprises a plurality of joints for specifically binding with the second biomolecule.

* * * * *